United States Patent

Rieber et al.

Patent Number: 5,576,462
Date of Patent: Nov. 19, 1996

[54] PREPARATION OF α-HYDROXYKETONES

[75] Inventors: Norbert Rieber, Mannheim; Joaquim H. Teles, Ludwigshafen, both of Germany

[73] Assignee: BASF Aktiengesellschaft, Ludwigshafen, Germany

[21] Appl. No.: 510,753

[22] Filed: Aug. 3, 1995

[51] Int. Cl.⁶ .................. C07C 49/395; C07C 49/403; C07C 49/497

[52] U.S. Cl. ........................... 568/341; 568/384

[58] Field of Search .................... 568/341, 384

[56] References Cited

U.S. PATENT DOCUMENTS

| | | | |
|---|---|---|---|
| 3,151,167 | 9/1964 | Eisenmann et al. | 568/341 |
| 3,505,360 | 4/1970 | Allison et al. | |
| 3,627,833 | 12/1971 | Tobias | 568/341 |
| 3,751,478 | 8/1973 | Tobias | 568/341 |
| 4,359,586 | 11/1982 | Ho et al. | 568/341 |
| 4,451,672 | 5/1984 | Grey | 568/384 |
| 4,532,358 | 7/1985 | Lukac et al. | 568/341 |
| 4,845,301 | 7/1989 | Sato et al. | 568/384 |

FOREIGN PATENT DOCUMENTS

| | | | |
|---|---|---|---|
| 0015216 | 2/1981 | Japan | 568/384 |
| 57-046933 | 3/1982 | Japan. | |

OTHER PUBLICATIONS

Houben–Weyl, vol. E13/1, pp. 64–71 (1988).
J. Am. Chem. Soc. 77, 5083–5089 (1955).
Bull. Chem. Soc. Japan, 48, 1337–1338 (1975).
Chem. Ber., 72, 1799–1804 (1939).

*Primary Examiner*—Joseph E. Evans
*Attorney, Agent, or Firm*—John H. Shurtleff

[57] ABSTRACT

A process for the preparation of α-hydroxyketones of the general formula I

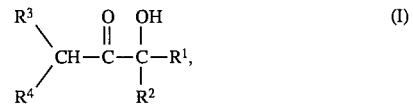

in which
$R^1$, $R^2$, $R^3$, and $R^4$ denote hydrogen or $C_1$–$C_8$ alkyl or
$R_1$ and $R^3$ together form a $C_2$–$C_{10}$ alkylene chain optionally mono- to tri-substituted by methyl and/or ethyl and
$R^5$ denotes hydrogen, methyl or ethyl,
from 2,3-epoxyalcohols of the general formula II

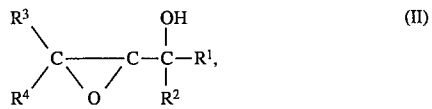

in which $R^1$, $R^2$, $R^3$, and $R^4$ have the above meanings, at temperatures of from −10° to 120° C. and pressures of from 0.01 to 20 bar in the presence of a catalyst, wherein the catalyst used is a hydridocobalt compound, and the preparation of 2,3-epoxyalcohols II from 3-hydroperoxy alkenes III and their preparation from alkenes IV using oxygen or gas mixtures containing oxygen.

10 Claims, No Drawings

PREPARATION OF α-HYDROXYKETONES

The present invention relates to a process for the preparation of α-hydroxyketones of 2,3-epoxyalcohols in the presence of a catalyst, in which the 2,3-epoxyalcohols can be obtained by the reaction of alkenes with oxygen or gas mixtures containing oxygen and chemical rearrangement of the resulting alkyl hydroperoxide in the presence of a catalyst.

The chemical rearrangement of epoxides to ketones using magnesium bromide etherate or boron trifluoride etherate as catalyst is described in *J. Am. Chem. Soc.* 77, 5083–5089 (1955). these catalysts are either ineffective or catalyze the polymerisation of the epoxyalcohol.

*Bull Chem. Soc. Japan,* 48, 1337 to 1338 (1975) discloses the chemical rearrangement of cyclohexenyl hydroperoxide to form 2,3-epoxycyclohexanol.

*Chem. Ber.,* 72, 1799 to 1804 (1939) describes the oxidation of cyclopentene to form cyclopentenyl hydroperoxide using photochemically excited oxygen giving poor yields. The uncatalyzed allylic oxidation of olefins to form allyl hydroperoxides is disclosed in *Houben-Weyl,* Vol E1 3/1,pp 64 to 71 (1988).

It is the object of the present invention to overcome the aforementioned drawbacks.

Accordingly, we have found a novel and improved process for the preparation of α-hydroxyketones of the formula I

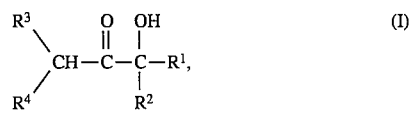

in which $R^1$, $R^2$, $R^3$, and $R^4$ denote hydrogen or $C_1$–$C_8$ alkyl or $R^1$ and $R^3$ together form a $C_2$–$C_{10}$ alkylene chain optionally mono- to tri-substituted by methyl and/or ethyl and from 2,3-epoxyalcohols of the formula II

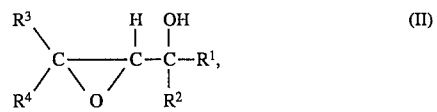

in which $R^1$, $R^2$, $R^3$, and $R^4$ have the above meanings, at temperatures of from –10° to 120° C. and pressures of from 0.01 to 20 bar in the presence of a catalyst, wherein the catalyst used is a hydridocobalt compound, and the preparation of 2,3-epoxyalcohols II from 3-hydroperoxy alkenes III and their preparation from alkenes IV using oxygen as taught below or gas mixtures containing oxygen.

The process of the invention can be carried out as follows.

Isomerization of 2,3-epoxycyclopentanol to 2-hydroxycyclopentanone 2,3-Epoxycyclopentanol II can be isomerized in substance or in solution in an inert solvent by treatment with a hydridocobalt compound as catalyst at temperatures of from –10° to 120° C., preferably from 20° to 100° C. and more preferably from 40° to 80° C. and pressures of from 0.01 to 20 bar, preferably from 0.1 to 5 bar and more preferably standard pressure (atmospheric pressure) to produce 2-hydroxycyclopentanone.

Suitable hydridocobalt compounds are those of the general formula HCoL$_4$, in which L stands for ligands having weak σ-donor properties and good π-acceptor properties, preferably CO, tri-($C_1$–$C_8$ alkyl)phosphites, arylphosphites, PF$_3$, or tris-(pentafluorophenyl)phosphine. Alternatively, the hydridocobalt compounds can be produced in situ by the reaction of dicobaltoctacarbonyl with protic compounds (e.g. alcohols or acids used as solvents or as co-catalyst, traces of water in the aprotic solvent, or the epoxyalcohol itself) or by the reaction of a tetracarbonyl cobaltate (e.g. sodiumtetracarbonyl cobaltate) with an acid (e.g. p-toluenesulfonic acid). the hydridocobalttetracarbonyl is preferably produced in situ from dicobaltoctacarbonyl.

The molar ratio of hydridocobalt compound to 2,3-epoxycyclopentanol II is usually from 0.001:1 to 2:1, preferably from 0.005:1 to 1:1 and more preferably from 0.01:1 to 0.5:1.

Examples of suitable inert solvents are alcohols such as $C_1$–$C_8$ alkanols, preferably $C_1$–$C_4$ alkanols such as methanol, ethanol, n-propanol, and isopropanol, benzene, alkylaromatics such as toluene, ortho-, meta-, and para-xylenes, carboxylic acids such as $C_1$–$C_8$ carboxylic acids, preferably $C_1$–$C_4$ carboxylic acids such as formic acid, acetic acid, and propionic acid, carboxylic acid esters such as $C_2$–$C_{12}$ carboxylates, preferably $C_2$–$C_6$ carboxylates such as methyl formate, ethyl formate, methyl acetate, ethyl acetate, methyl propionate and ethyl propionate. Particularly methanol and benzene are preferred solvents.

Isomerization of cyclopentenyl hydroperoxide to form 2,3-epoxycyclopentanol

Cyclopentenyl hydroperoxide III can be isomerized in the presence of a soluble compound of a transition metal in Group IVb, Vb, or VIb at temperatures of from –20° to 120° C., preferably from 20° to 100° C. and more preferably from 40° to 90° C. and pressures of from 0.01 to 20 bar, preferably from 0.1 to 5 bar and more preferably standard pressure (atmospheric pressure) to form 2,3-epoxycyclopentanol.

Suitable catalysts containing transition metals in Groups IVb, Vb, and VIb are compounds of the elements titanium, zirconium, hafnium, vanadium, niobium, tantalum, chromium, molybdenum, and tungsten, preferably titanium, vanadium, and molybdenum compounds, more preferably vanadium compounds. Good results can be achieved, for example, using vanadyl acetylacetonate [VO(acac)$_2$] or using vanadyl trialkoxylates [VO(OR)$_3$], in which R stands for $C_1$–$C_{12}$ alkyl, preferably $C_1$–$C_8$ alkyl, more preferably $C_1$–$C_4$ alkyl such as methyl, ethyl, n-propyl, isopropyl, n-butyl, isobutyl, sec-butyl, and tert-butyl or aryl such as phenyl, 2-methoxyphenyl, 1-naphthyl, and 2-naphthyl, preferably phenyl, more preferably isopropyl and tert-butyl.

Suitable inert solvents are, for example, chlorinated hydrocarbons such as dichloromethane, chloroform, and 1,1,1-trichloromethane, ethers such as tetrahydrofuran, aromatics such as benzene and toluene or hydrocarbons such as cyclohexane, esters of $C_1$–$C_4$ carboxylic acids with $C_1$–$C_4$ alcohols such as ethyl acetate oder $C_2$–$C_{12}$ nitriles such as acetonitrile or benzonitrile.

The molar ratio of catalysts containing transition metals in Groups IVb, Vb, and VIb to the cyclopentyl hydroperoxide III is usually from 0.00001:1 to 0.1:1, preferably from 0.0005:1 to 0.05:1 and more preferably from 0.001:1 to 0.01:1.

The addition of a water acceptor such as anhydrous sodium sulfate can accelerate the reaction. The addition of an acid acceptor such as calcium oxide or barium oxide can reduce the formation of by-products.

The reaction time is usually set such that a hydroperoxide conversion between 50 and 100% is achieved. To facilitate final purification, the reaction is preferably run to a conversion of >90%.

Oxidation of cyclopentene to form cyclopentenyl hydroperoxide

Cyclopentene IV can be oxidized in substance or in the form of a mixture with less readily oxidizable substances using oxygen or a gas mixture containing oxygen, such as air, in a suitable reactor, e.g., a bubble-cap column or a stirred boiler equipped with a stirrer suitable for mixing gases and liquids at temperatures ranging from 20° to 120° C., preferably from 35° to 90° C., and more preferably from 40° to 80° C. to form cyclopentenyl hydroperoxide III.

The pressure is not a critical parameter in this reaction. The overall pressure in the reactor should be usually greater than the vapor pressure of the liquid components at the temperature of reaction.

Usually, no catalyst is required for this oxidation. During oxidation, acid acceptors can be added, e.g., alkali metal or alkaline earth metal carbonates, alkali metal or alkaline earth metal hydrogen carbonates or alkali metal or alkaline earth metal carboxylates.

The reaction time or residence time is usually set such that the cyclopentene conversion is between 1 and 70%. Cyclopentene conversions between 10 and 20% are particularly preferred.

Further processing is advantageously effected by separating the unconverted cyclopentene and either isolating the cyclopentenyl hydroperoxide or causing it to be taken up in an inert solvent.

The substituents $R^1$, $R^2$, $R^3$, and $R^4$ in the compounds I, II, III, and IV have the following meanings:

$R^1$, $R^2$, $R^3$, and $R^4$ independently denote hydrogen, $R^1$ and $R^3$ when taken together form a $C_2$–$C_{10}$ alkylene chain optionally mono- to tri-substituted by methyl and/or ethyl.

EXAMPLES

Example 1

Batch oxidation of cyclopentene to form cyclopentenyl hydroperoxide using oxygen under elevated pressure 150 g of stabilizer-free cyclopentene and 3 g of cyclopentenyl hydroperoxide (ca 80% strength) were placed in a glass autoclave having a capacity of 400 mL and equipped with a stirrer, oxygen inlet, and pressure control means. The autoclave was then brought to the desired temperature by means of an oil bath. Oxygen was then metered in under controlled pressure. After a predetermined period of time, the experiments were stopped and the contents of the reactor were analyzed. The influence of temperature and pressure on conversion and selectivity is shown in the following tables.

TABLE 2

Influence of the overall pressure at constant temperature (70° C.) and reaction time (4 h)

| Pressure [bar] | % Conversion | % Selectivity |
| --- | --- | --- |
| 4 | 23.0 | 84.0 |
| 6 | 23.2 | 80.4 |
| 8 | 21.4 | 81.8 |

Example 2

Continuous oxidation of cyclopentene to form cyclopentenyl hydroperoxide using oxygen under standard pressure A bubble-cap column having a capacity of 1 L and equipped with a double-walled jacket and a mounted reflux condenser was filled with ca 750 mL of pre-oxidized cyclopentene (ca 15 wt % of cyclopentenyl hydroperoxide), which was maintained thermostatically at ca 40° C. and oxidized with a steady stream of oxygen (5 L/min). through an opening in the lower quarter of the bubble-cap column fresh stabilizer-free cyclopentene was continuously metered in by means of an HPLC pump. The product was continuously removed through an overflow in the upper portion of the bubble-cap column. At a cyclopentene conversion of 31.5 mL/h the product contains from 19 to 20 wt % of cyclopentenyl hydroperoxide (equivalent to a conversion of approximately 16% and a selectivity of approximately 88%). the unconverted cyclopentene can be withdrawn at room temperature using a rotation evaporator. The residues contain ca 90 wt % of hydroperoxide as a colorless liquid. The remaining 10% consists for the most part of cyclopentenone and cyclopentenol. The cyclopentene which distills off is almost pure and can be returned to the bubble-cap column.

Example 3

Oxidation of cyclohexene to form cyclohexenyl hydroperoxide using oxygen under standard pressure in a bubble-cap column A bubble-cap column having a capacity of 5 L and equipped with a double-walled jacket and a reflux condenser was filled with ca 3 L of cyclohexene, which was maintained thermostatically at ca 80° C. and oxidized with a steady

TABLE 1

Influence of temperature of reaction and reaction time at constant pressure (P = 6 bar)

| | T = 60° C. | | T = 70° C. | | T = 80° C. | |
| --- | --- | --- | --- | --- | --- | --- |
| Time h | % Conversion | % Selectivity | % Conversion | % Selectivity | % Conversion | % Selectivity |
| 1 | | | 4.7 | 79.6 | 8.8 | 83 |
| 2 | | | 8.8 | 74.4 | 27.2 | 73.4 |
| 3 | | | 15.4 | 82.9 | 42.5 | 65.2 |
| 4 | 3.6 | 91.1 | 23.2 | 80.4 | 51.3 | 56.2 | stream of oxygen (10 L/min). Following a period of 7 h, the hydroperoxide content had risen to 9.2% and the acid number was 0.1 g KOH/g. After a further 3.5 h the hydroperoxide content had risen to 17.1% and the acid number to 0.74 g KOH/g. The effluent was washed with 10% strength sodium carbonate solution (acid number after washing: 0.15 g KOH/g), and the organic phase was dried over sodium sulfate and concentrated. 513 g of crude cyclohexenyl hydroperoxide (content: ca 75%, determined by titration) remained as residue. This hydroperoxide can be used directly for the second step.

Example 4

Catalysts for the rearrangement of cyclopentenyl hydroperoxide to form 2,3-epoxycyclopentanol In a three-necked flask having a capacity of 1 L, the catalyst was dissolved in 100 g of solvent (cf Table 3) and brought to reflux temperature. A solution of 50 g of cyclopentenyl hydroperoxide (as crude hydroperoxide having a content of from ca 85 to 95%) in 50 g of solvent was then added dropwise through a dripping, funnel over a period of one hour. The reaction was monitored by titration of the hydroperoxide. Usually the reaction was stopped when the hydroperoxide content was less than 1%. The content of product in the effluent was determined by means of quantitative gas chromatography and the effluent was then distilled in a falling film evaporator. The distillate (free from catalyst and high-boiling fractions) can be fractionally distilled. The results achieved with various catalysts are summarized in Table 3 below.

Example 6

Chemical rearrangement of cis-2,3-epoxycyclopentanol to form glutaroin using dicobaltoctacarbonyl 3 g of crude 2,3-epoxycyclopentanol (content of epoxycyclopentanol ca 88%, ca 95% thereof cis) were dissolved in 20 mL of dry benzene. 0.18 g of solid dicobaltoctacarbonyl were then added in a single portion and the mixture was stirred for 24 h at 50° C. under nitrogen. After this period of time, ca 40% of the cis-2,3-epoxycyclopentanol had reacted and the selectivity toward glutaroin was 80%.

Example 7

Chemical rearrangement of cis-2,3-epoxycyclopentanol to form glutaroin using sodium tetracarbonyl cobaltate and acid Sodium tetracarbonyl cobaltate (in the form of a solution in THF) was prepared by the method proposed by Edgell and Lyford (*Inorg. Chem.*, 9, 1932 to 1933 (1970)) from 1.68 g of dicobaltoctacarbonyl, 2.5 g of NaOH and 20 mL of THF. 5 g of crude 2,3-epoxycyclopentanol (content of epoxycyclopentanol ca 70%, ca 95% thereof being cis) and 0.55 g of p-toluenesulfonic acid were dissolved in 20 mL of toluene,

TABLE 3

| Catalyst | Quantity [mol %] | T [C.] | Time [h] | Solvent | Conversion [%] | Selectivity [%] | cis/trans |
|---|---|---|---|---|---|---|---|
| B(OMe)$_3$ | 0.5 | 67 | 6 | THF | <1 | | |
| Al(OiPr)$_3$ | 0.5 | 67 | 6 | THF | <1 | | |
| Ti(OiPr)$_4$ | 1 | 67 | 54 | THF | 72 | 31 | 1.1 |
| Ti(OiPr)$_4$ | 2.5 | | | | | | |
| L-Diisopropyl tartrate | 1.5 | 67 | 21 | THF | 77 | 48 | 0.6 |
| Zr(OiPr)$_4$·iPrOH | 0.05 | 67 | 23 | THF | <10 | | |
| Hf(OiPr)$_4$ | 0.05 | 67 | 5 | THF | <10 | | |
| VO(acac)$_2$ | 0.025 | 80 | 18 | benzene | 96 | 65 | 27.5 |
| VO(OiPr)$_3$ | 0.005 | 67 | 23 | THF | 94 | 70 | 22.9 |
| VO(OiPr)$_3$ | 0.005 | | | | | | |
| CaO | 0.25 | 67 | 23 | THF | 93 | 82 | 17.0 |
| Nb(OEt)$_5$ | 0.05 | 67 | 23 | THF | <10 | | |
| NH$_4$·Nb(oxalate)$_3$ | 2.5 | 67 | 23 | THF | 43 | 2 | 0.9 |
| Ta(OEt)$_5$ | 0.05 | 67 | 23 | THF | <10 | | |
| Cr(acac)$_3$ | 0.05 | 67 | 23 | THF | 75 | 7 | 1.0 |
| MoO$_2$(acac)$_2$ | 0.05 | 67 | 23 | THF | 71 | 58 | 3.1 |
| Mo(CO)$_6$ | 0.05 | 67 | 23 | THF | 67 | 75 | 1.2 |
| W(CO)$_6$ | 0.05 | 67 | 23 | THF | 86 | 15 | 0.9 |
| Bu$_2$SnO | 0.5 | 67 | 6 | THF | <1 | | |

Example 5

Chemical rearrangement of cis-2,3-epoxycyclopentanol to form glutaroin by means of dicobaltoctacarbonyl and acid 3 g of crude 2,3-epoxycyclopentanol (content of epoxycyclopentanol ca 90%, ca 95% thereof being cis) were dissolved in 20 mL of dry toluene. 0.3 g of solid dicobaltoctacarbonyl and 0.09 g of p-toluenesulfonic acid were then added in a single portion and the mixture was stirred over a period of 21 h at 50° C. under nitrogen. After this period of time, approximately two thirds of the epoxyalcohol had reacted and the selectivity toward glutaroin was 70%. There were added another 0.3 g of solid dicobaltoctacarbonyl and the mixture was stirred for a further 5 h at 50° C. The cis-2,3-epoxycyclopentanol had then converted to an extent of 93%. The trans-2,3-epoxycyclopentanol remained virtually unchanged. The selectivity toward glutaroin was 52%. The reaction mixture was then extracted with water. An almost cobalt-free solution of glutaroin in water was obtained.

degassed, and heated to 60° C. There were then added 15 mL of the sodium tetracarbonyl cobaltate solution and the mixture was stirred for 43 h at 60° C. Conversion: 42%, selectivity: 85% (as determined by gas chromatography).

Example 8

Chemical rearrangement of cis-2,3-epoxycyclohexanol to form adipoin (2-hydroxycyclohexanone)

3 g of crude 2,3-epoxy cyclohexanol (content of epoxy cyclohexanol ca 50%, ca 95% thereof being cis), 0.3 g of dicobaltoctacarbonyl and 0.09 g of p-toluenesulfonic acid were dissolved in 20 mL of toluene and the mixture was stirred for 21 h at 50° C. under nitrogen. Conversion of cis-2,3-epoxycyclohexanol: 95%; selectivity toward adipoin: 80%.

Comparative Example 9

(As per *J. Org. Chem.*, 36, 3135–8 (1971)

Chemical rearrangement of 2,3-epoxycyclopentanol to form glutaroin using LiBr/RbBr on Al$_2$O$_3$ 20 g of epoxycyclopentanol (content of epoxycyclopentanol ca 70%, ca 95% thereof cis) were slowly evaporated and passed, at 270° C. (5 mbar), over LiBr/RbBr on Al$_2$O$_3$ (14.1 g of LiBr and 15.9 g of RbBr on 90 g of Al$_2$O$_3$-catalyst described in the literature as being suitable for the gas-phase isomerization of epoxides to ketones). The distillate (19.2 g) contained ca 10% of glutaroin. The main product was cyclopenten-2-one.

Comparative Example 10

(As per *J. Am. Chem. Soc.*, 77, 5083–9 (1955))

Chemical rearrangement of 2,3-epoxycyclopentanol to form glutaroin using magnesium bromide etherate Magnesium bromide etherate is described in the literature as being a choice reagent for the isomerization of epoxides to ketones (*J. Am. Chem. Soc.*, 77, 5083 to 5089 (1955)). 2 g of epoxycyclopentanol (content of epoxycyclopentanol ca 90%, ca 95% thereof being cis) were dissolved in 10 mL of diethyl ether, and 3.4 g of magnesium bromide etherate were added. Following a period of 30 minutes at 20° C., the educt was completely converted. Mainly non-volatile products were formed. Only traces of glutaroin were produced.

Comparative Example 11

(As per *J. Am. Chem. Soc.*, 77, 6525–32 (1955)

Conversion of 2,3-epoxycyclopentanol to glutaroin using boron trifluoride etherate Boron trifluoride etherate has likewise been described in the literature a number of times as being an agent for the isomerization of epoxides to ketones If solutions of 2,3-epoxycyclopentanol are treated in toluene with from 0.1 to 10 mol % of boron trifluoride etherate at room temperature, viscous polymers separate after a short time (great care should be taken here, as the reaction is strongly exothermal). Glutaroin could not be identified as a product.

Comparative Example 12

(As per *Houben-Weyl*, Vol VII/2a, 932–42 (1973), Vol VI/3, 431–41 (1965) and Vol VII/1, 237–9 (1954)

Experiments for chemically rearranging 2,3-epoxycyclopentanol using other catalysts disclosed in the literature The following catalysts, some of which are described in the literature as being suitable for the isomerization of epoxides to ketones, were found to be inactive for the isomerization of 2,3-epoxycyclopentanol to glutaroin:

Co$_2$(CO)$_6$(PBu$_3$)$_2$, RhCl(PPh$_3$)$_3$, Mo(CO)$_6$, RuCl$_2$(PPh$_3$)$_3$, RhH(CO)(PPh$_3$)$_3$, LiBr/HMPA, LiClO$_4$, RuH$_2$(PPh$_3$)$_4$, Mn$_2$(CO)$_{10}$, Pd on supports, Pd(PPh$_3$)$_4$, Rh$_6$(CO)$_{16}$, and ZnCl$_2$.

We claim:

1. A process for the preparation of an α-hydroxyketone of the formula

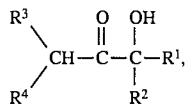

wherein each of R$^1$, R$^2$, R$^3$ and R$^4$ represents hydrogen or C$_1$–C$_8$-alkyl and R$^1$ and R$^3$ when taken together may also form a C$_2$–C$_{10}$-alkylene chain optionally mono- to tri-substituted by methyl and/or ethyl, which process comprises:

catalytically reacting a 2,3-epoxyalcohol of the formula

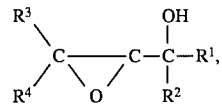

wherein R$^1$, R$^2$, R$^3$ and R$^4$ have the above meanings, at a temperature of from −10° C. to 120° C. and a pressure of from 0.01 to 20 bar in the presence of a hydridocobalt compound acting as the catalyst.

2. A process as claimed in claim 1, wherein the catalyst is a compound of the formula HCoL$_4$ in which L stands for CO, a tri-(C$_1$–C$_8$-alkyl)phosphite, an arylphosphite, PF$_3$ or tris(pentafluorophenyl)phosphine or mixtures thereof.

3. A process as claimed in claim 1, wherein the catalytic reaction is carried out at temperatures from 20° to 100° C. and pressures of from 0.1 to 5 bar.

4. A process as claimed in claim 1, wherein the catalytic reaction is carried out at temperatures from 40° to 80° C. and under atmospheric pressure.

5. A process as claimed in claim 1, wherein the catalytic reaction is carried out in the presence of an inert solvent.

6. A process as claimed in claim 5, wherein the inert solvent is selected from the group consisting of C$_1$–C$_4$-alkanols and benzene.

7. A process as claimed in claim 1, wherein the required 2,3-epoxyalcohol reactant II is first prepared by a process which comprises catalytically reacting a 3-hydroperoxy alkene of the formula

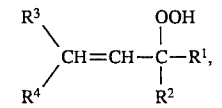

wherein R$^1$, R$^2$, R$^3$ and R$^4$ have the meanings given in claim 5, at a temperature of from −10° C. to 120° C. and a pressure of from 0.01 to 20 bar in the presence of a compound of a transition metal of Groups IVb, Vb or VIb of the Periodic Table of Elements acting as the catalyst.

8. A process as claimed in claim 7, wherein said transition metal of the catalyst is selected from the group consisting of titanium, vanadium and molybdenum.

9. A process as claimed in claim 7, wherein the transition metal catalyst is a vanadium compound.

10. A process as claimed in claim 7, wherein the intermediate 3-hydroperoxy alkene III is first obtained in preliminary step which comprises reacting an alkene of the formula

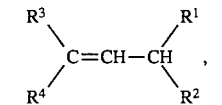

wherein R$^1$, R$^2$, R$^3$ and R$^4$ have the meanings given in claim 5, with oxygen or an oxygen containing gas at a temperature of from 20° to 120° C. and a pressure of from 0.01 to 20 bar, and the resulting 3-hydroperoxy alkene III product is then used directly in the catalytic process of claim 7.

\* \* \* \* \*

UNITED STATES PATENT AND TRADEMARK OFFICE
CERTIFICATE OF CORRECTION

PATENT NO. : 5,576,462
DATED : Nov. 19, 1996
INVENTOR(S) : Rieber et al.

It is certified that error appears in the above-indentified patent and that said Letters Patent is hereby corrected as shown below:

ON THE COVER PAGE:

In the ABSTRACT:

In line 3, following formula (I): change "$R_1$" to -- $R^1$ --.

Signed and Sealed this

Twenty-sixth Day of May, 1998

Attest:

BRUCE LEHMAN

*Attesting Officer*  *Commissioner of Patents and Trademarks*